(12) United States Patent
Wang et al.

(10) Patent No.: US 9,487,745 B2
(45) Date of Patent: *Nov. 8, 2016

(54) MICRO-PATTERNED PLATE COMPOSED OF AN ARRAY OF RELEASABLE ELEMENTS SURROUNDED WITH SOLID OR GEL WALLS

(75) Inventors: Yuli Wang, Cary, NC (US); Nancy Allbritton, Chapel Hill, NC (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 720 days.

This patent is subject to a terminal disclaimer.

(21) Appl. No.: 12/670,365

(22) PCT Filed: Jul. 25, 2008

(86) PCT No.: PCT/US2008/071245
§ 371 (c)(1),
(2), (4) Date: May 24, 2010

(87) PCT Pub. No.: WO2009/018167
PCT Pub. Date: Feb. 5, 2009

(65) Prior Publication Data
US 2010/0285992 A1    Nov. 11, 2010

Related U.S. Application Data

(60) Provisional application No. 60/952,333, filed on Jul. 27, 2007.

(51) Int. Cl.
C12M 1/20     (2006.01)
C12N 11/14    (2006.01)
(Continued)

(52) U.S. Cl.
CPC .............. *C12M 1/20* (2013.01); *C12M 3/00* (2013.01); *C12M 23/22* (2013.01); *C12M 23/44* (2013.01);
(Continued)

(58) Field of Classification Search
CPC ...... C12M 1/20; C12M 25/06; C12M 23/44; C12M 23/22; C12M 3/00; C12N 11/14; C12N 11/02; C12N 1/02; C12N 5/00
See application file for complete search history.

(56) References Cited

U.S. PATENT DOCUMENTS 5,998,129 A    12/1999    Schutze et al.
6,090,919 A    7/2000     Cormack et al.
(Continued)

FOREIGN PATENT DOCUMENTS

WO    WO 97/29355 A1    8/1997
WO    WO 02/094454 A1   11/2002
(Continued)

OTHER PUBLICATIONS

Koh et al., Biomedical Microdevices, 2003, 5(1):11-19.*
(Continued)

*Primary Examiner* — Jeremy C Flinders
(74) *Attorney, Agent, or Firm* — One LLP (57) ABSTRACT

A micro-patterned plate composed of an array of releasable elements surrounded by a gel or solid wall and methods of manufacture of the micropatterned plate. The surface properties of walls can be tailored if needed to be repellent or attracting to proteins. The walls can also inhibit cell attachment. The walls enable cells or other materials to be localized to the tops of the releasable elements. The individual element in the array of releasable elements can be released from the array by a mechanical force.

8 Claims, 4 Drawing Sheets

(51) Int. Cl.
    *C12N 11/02*     (2006.01)
    *C12M 3/00*     (2006.01)
    *C12M 1/00*     (2006.01)
    *C12M 1/12*     (2006.01)
    *C12N 1/02*     (2006.01)
    *C12N 5/00*     (2006.01)

(52) U.S. Cl.
    CPC .............. *C12M 25/06* (2013.01); *C12N 11/02* (2013.01); *C12N 11/14* (2013.01); *C12N 1/02* (2013.01); *C12N 5/00* (2013.01)

(56) References Cited

U.S. PATENT DOCUMENTS

| | | |
|---|---|---|
| 6,529,835 B1 | 3/2003 | Wada et al. |
| 2001/0006815 A1 | 7/2001 | Rabbani et al. |
| 2001/0048977 A1 | 12/2001 | Dorozhkina et al. |
| 2001/0055882 A1 | 12/2001 | Ostuni et al. |
| 2002/0119578 A1 | 8/2002 | Zaffaroni et al. |
| 2003/0059764 A1 | 3/2003 | Ravkin et al. |
| 2003/0129741 A1 | 7/2003 | Ramstad |
| 2004/0028875 A1 | 2/2004 | Van Rijn et al. |
| 2004/0067596 A1 | 4/2004 | Halverson et al. |
| 2004/0087052 A1 | 5/2004 | Kalakis et al. |
| 2004/0171135 A1 | 9/2004 | Ostuni et al. |
| 2005/0277053 A1 | 12/2005 | Platzer et al. |
| 2006/0013031 A1 | 1/2006 | Ravkin et al. |
| 2006/0121500 A1 | 6/2006 | Bachman et al. |
| 2007/0128716 A1 | 6/2007 | Wang et al. |
| 2007/0161100 A1 | 7/2007 | Tanaka et al. |
| 2007/0166816 A1* | 7/2007 | Campbell et al. ......... 435/288.4 |
| 2007/0238122 A1 | 10/2007 | Allbritton et al. |
| 2007/0292312 A1 | 12/2007 | Bachman et al. |

FOREIGN PATENT DOCUMENTS

| | | |
|---|---|---|
| WO | WO 03/016868 A1 | 2/2003 |
| WO | WO 03/035824 A1 | 5/2003 |
| WO | WO 03/039750 A1 | 5/2003 |
| WO | WO 2004/024328 A1 | 3/2004 |
| WO | WO 2006/041938 A1 | 4/2006 |
| WO | WO 2006/060922 A1 | 6/2006 |

OTHER PUBLICATIONS

Salmon et al., Proc. Natl. Acad. Sci., 1993, 90:11708-11712.*
Revzin et al. (Langmuir, 2003, 19:9855-9862).*
Pregibon et al. (Langmuir, 2006, 22:5122-5128).*
US, Office Action (U.S. Appl. No. 11/733,053), Aug. 18, 2008.
WO, International Search Report and Written Opinion, Sep. 26, 2008.
WO, International Search Report and Written Opinion, Oct. 15, 2008.
US, Office Action (U.S. Appl. No. 11/243,926), Oct. 20, 2008.
US, Office Action (U.S. Appl. No. 11/243,926), Mar. 16, 2009.
EP, Supplemental Search Report (05802866.3), May 7, 2009.
US, Office Action (U.S. Appl. No. 11/733,053), Sep. 10, 2009.
US, Office Action (U.S. Appl. No. 11/539,695), Dec. 4, 2009.
Hexion Specialty Chemicals, Technical Data Sheet, EPON Resin 1002F, http://www.resins.com/resins/am/pdf/RP3063.pdf 2005.
Barron et al., "Laser Printing of Single Cells: Statistical Analysis, Cell Viability, and Stress," Annals of Biomedical Engineering, 33:2, pp. 121-130 (Feb. 2005).
Langer et al., "Live cell catapulting and recultivation does not change the karyotype of HCT116 tumor cells," Cancer Genetics an Cytogenetics, No. 161 pp. 174-177 (2005).
Stich et al., "Live Cell Catapulting and Recultivation," Pathology Research and Practice, 199:6, pp. 405-409 (Jan. 1, 2003).
Watson, Molecular Biology of the Gene, Third Edition, W.A. Benjamin, Inc., Menlo Park, CA, 1976, p. 62.
Zoeller et al., Strategies for Isolating Somatic Cell Mutants Defective in Liquid Biosynthesis, Methods of Enzymology, vol. 2, pp. 34-51 (1992).

* cited by examiner

MICRO-PATTERNED PLATE COMPOSED OF AN ARRAY OF RELEASABLE ELEMENTS SURROUNDED WITH SOLID OR GEL WALLS

The invention was made with government support under grant EB004597 awarded by the National Institutes of Health. The government has certain rights in the invention.

FIELD

The present invention relates to a micro-patterned plate composed of an array of releasable elements, and, more particularly, to a micropatterned plate composed of an array of releasable elements surrounded by a gel or solid wall.

BACKGROUND

The ability to pattern and then release biomolecules, cells, tissues, organisms, colonies, embryos, and other biological samples at specific sites on a plate is important for many areas of scientific research and medicine. By placing such samples at known locations, researchers may study many samples under identical and controlled conditions, while monitoring each sample independently and repeatedly over time. Since each sample is in a known location, large numbers of samples may be studied, resulting in statistically significant data sets. Arrays of isolated biological samples can be used to assist in diagnosis by observing the samples under controlled conditions in the presence of unknown agents or pathogens. Furthermore, it has additional advantages if the samples on specific location can be isolated from the array. Release and collection permits the patterned material to be analyzed further as well as by a variety of other techniques.

To accomplish patterning combined with release of biological samples, conventional technologies rely on four major strategies: (1) patterned surface treatments on a flat plate, (2) structured microwells, (3) physical stenciling, (4) a micro-bubble plate, all of which have shortcomings overcome by the embodiments described herein. Only the microbubble plate permits release of the arrayed samples.

(1) Patterned surface treatments on a flat plate create surfaces with specific chemistry at predetermined locations. This is performed by lithographic methods (i.e., UV radiation through a photographic mask), or by rubber stamp approaches, where chemicals are physically transferred to the plate surface by a patterned rubber stamp. The result of surface treatments is that regions are made favorable or unfavorable for sample attachment (e.g., cell growth, protein binding). After incubation with the media, the media and buffer are washed away. These methods are not highly selective—patterning of the media is not particularly good, and each media/plate requires a different surface treatment specific to that media/plate combination. In addition, the samples attached on specific location can not be isolated from the array.

(2) Structured microwells may be patterned into the surface by lithographic etching, lithographic photopolymerization or molding cavities in the surfaces. Such microwells are of limited use because cells will readily grow out of the cavities and media may readily coat all sides of the microwells. For best results, high aspect ratio wells are required (to contain the biological media), increasing manufacturing difficulty and cost. In addition, the samples attached inside a specific microwell can not be isolated from the array.

(3) Physical stenciling techniques use a rigid temporary barrier that is placed over the plate of interest. This barrier is in the form of a stencil or microfluidic device. Following this, media is introduced and allowed to attach to the surface at locations allowed by the stencil. After attachment, the stencil is removed leaving patterned media. This method suffers because it is difficult (and expensive) to produce stencils of high resolution, with large numbers of precision holes. The stencils must remain in intimate contact with the surface during the entire period of incubation (attachment). Generally, stencils leak between openings further reducing pattern resolution. Finally, such stencils are expensive, and a single stencil must be used for the entire incubation period for each surface that is to be patterned. In addition, the samples attached on a specific location cannot be isolated from the array.

(4) A micro-bubble plate is an array of releasable micropallets with the cavities that trap gas, usually in the form of bubbles, when the plate is submerged in liquid. Gas bubbles provide contiguous, impenetrable barriers blocking access of biological sample to the cavities. Biological samples placed on the array are forced to attach only on the tops of the micropallets, i.e., the surfaces wetted by aqueous media. In addition, the samples attached on a specific micropallet can be isolated from the array by a mechanical force generated by a focused laser pulse. However, the micro-bubble plate has several limitations. In order to trap air bubbles, a hydrophobic silane layer is coated on the surface of the plate. The trapped air tends to become unstable in some micropallet geometries, such as in big cavities. The trapped air tends not to be stable on a long term in some wetting solutions, such as in pure water, in solution with low surface tension, and in some protein solutions.

SUMMARY

Embodiments disclosed herein are directed to a micro-patterned plate composed of an array of releasable elements surrounded by a gel or solid wall and methods of manufacture of the micro-patterned plate. The surface properties of walls can be tailored if needed to be repellent or attracting to proteins. The walls can also inhibit cell attachment. The walls enable cells or other materials to be localized to the tops of the releasable elements. Even though surrounded by walls, the individual element in the array of releasable elements can be released from the array by a mechanical force.

This micro-patterned plate with its array of releasable elements surrounded by a gel or solid wall provides a platform for performing high speed, addressable analysis of biological and chemical samples, as well as an efficient method for isolating subsets of samples from a larger population of samples. The embodiments described herein enable the plating of cells and tissues at specific sites especially on an array, and can be used to coat the surface of a plate with coatings at specific locations for patterned coating applications.

Other systems, methods, features and advantages of the invention will be or will become apparent to one with skill in the art upon examination of the following figures and detailed description.

BRIEF DESCRIPTION DRAWINGS

The details of the invention, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DESCRIPTION

Each of the additional features and teachings disclosed below can be utilized separately or in conjunction with other features and teachings to produce a micropatterned plate composed of an array of releasable elements surrounded by a gel or solid wall. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

The various embodiments and examples provided herein were described in U.S. Provisional application No. 60/952,333, which is incorporated herein by reference.

Figure 1:
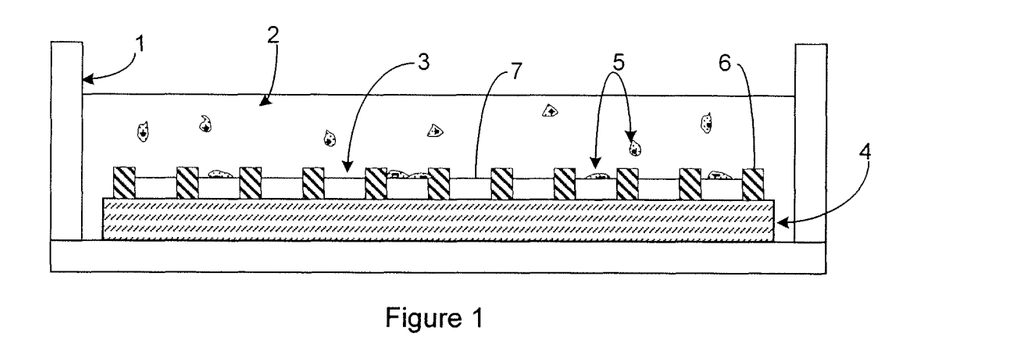
FIG. 1 is a diagram showing cross-sectional view of the micro-patterned plate submerged in a solution in a container.
Figure 2:
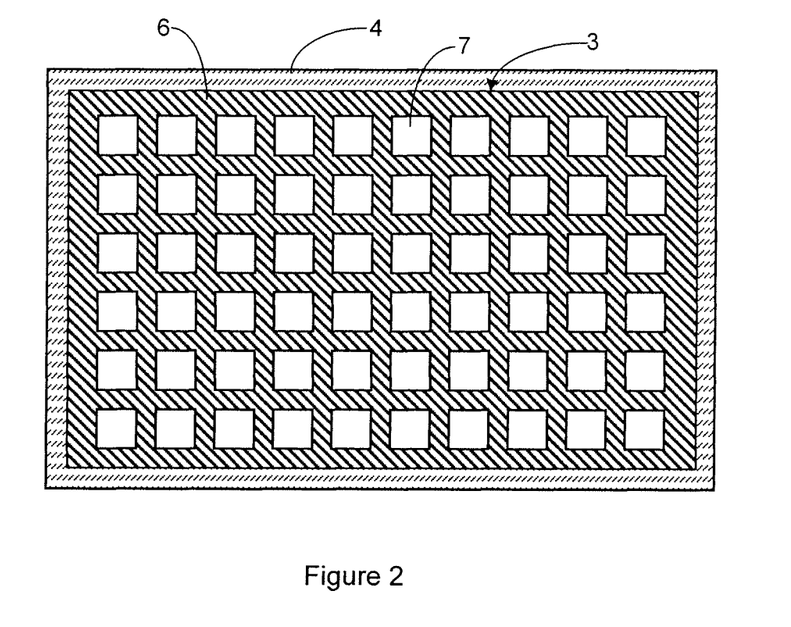
FIG. 2 is a diagram showing a top view of the micro-patterned plate.

The various embodiments and examples provided herein are generally directed to, as depicted in FIGS. 1 and 2, a novel micro-patterned plate 3 composed of an array of releasable elements 7 surrounded by solid or gel walls 6. For the purpose of discussion, the small releasable elements 7 will be referred to as "micropallets". The micro-patterned plate 3 enables high speed, addressable analysis of biological and chemical samples, as well as an efficient method for isolating subsets of samples from a larger population of samples. The surface properties of the walls 6 are themselves, or are modified to be, repellent (or attracting) to protein adsorption and cell attachment and therefore help to localize biomolecule attachment or cell growth on only the top surface of micropallets 7. Even though surrounded by the walls 6, the individual micropallets 7 can be released from the array by a mechanical force. As a result, the micro-patterned plate 3 provides a platform for performing high speed, addressable analysis of biological and chemical samples, as well as an efficient method for isolating subsets of samples from a larger population of samples.

The fabrication of a plate of micropallets has been disclosed in U.S. application Ser. No. 11/742,006 which is incorporated herein by reference. In brief, a plate of micropallets can be manufactured by optical lithography and a photosensitive polymer, or by optical lithography and etching, or by the use of a stencil, or by the use of a laser, or by the use of machining material, or by the use of molding a polymer.

Figure 4:
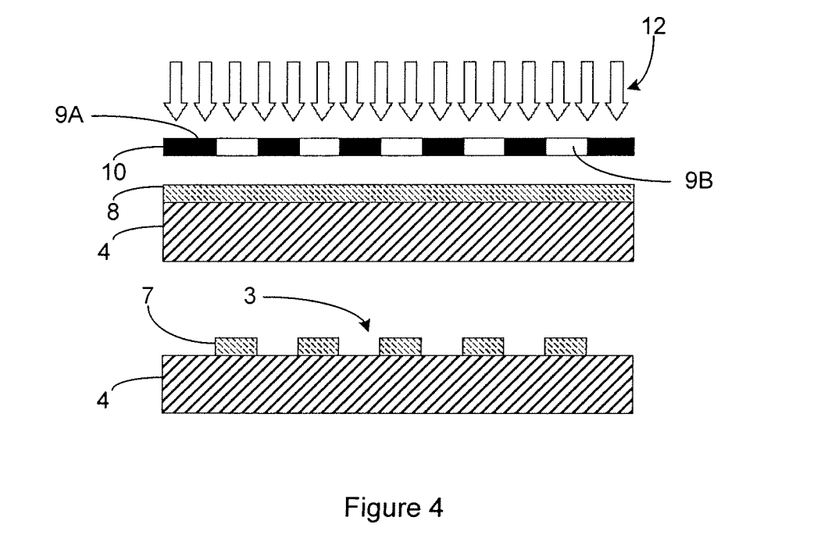
FIG. 4 is a diagram of basic process flow for producing a micro-patterned plate having a micropallet array FIG. 5 are optical (A, B) and SEM (C, D) images of a micropallet array.

As depicted in the FIG. 4, the process to manufacture a plate 3 of micropallets 7 includes placing a film layer 8 of a photosensitized solvent mixture on the surface of a substrate 4 such as glass or the like by any convenient means including spinning, painting, dipping, pouring, casting, and the like. The solvent is dried off to leave a semi-dry film 8 of the monomer. The film layer 8 may be further processed at this point, for example by planarizing, cutting, embossing, and the like. This film layer 8 is exposed through a mask 10 to UV light 12, preferably approximately 365 nm in wavelength, although most UV wavelengths will suffice. The mask 10 has regions that are opaque 9A and transparent 9B to the UV light 12, thus only certain regions of the film layer 8 are exposed to UV light 12. The exposed regions are cross-linked by the UV light 12 and a photoacid generator in the material of the film layer 8.

After exposure, the film 8 is "post baked" by raising the temperature of the film layer 8. Various temperatures may be used, but in a preferred embodiment the post bake temperature is approximately 95° C. Higher temperatures risk linking unexposed portions of the film layer 8. After post-bake, the film layer 8 is washed in a solvent bath to strip away the portions of the film that were not linked, leaving behind solid structures 7 of the linked monomer that reproduce the shape of the transparent regions of the mask 10. The solid structures 7 of linked monomer may be further processed at this point.

A plate of micropallets surrounded with gas bubble walls has been disclosed in U.S. application Ser. No. 11/536,965 which is incorporated herein by reference. The gas bubbles are trapped in the cavities between the micropallets, thus forming a continuous gas walls to surround the micropallets. The gas bubbles help to localize the attachment of biological materials (such as biomolecules or cells) and non-biological materials only on the top surface of micropallets. The embodiments described herein can be used to create gel or solid walls in place of air walls.

Figure 3:
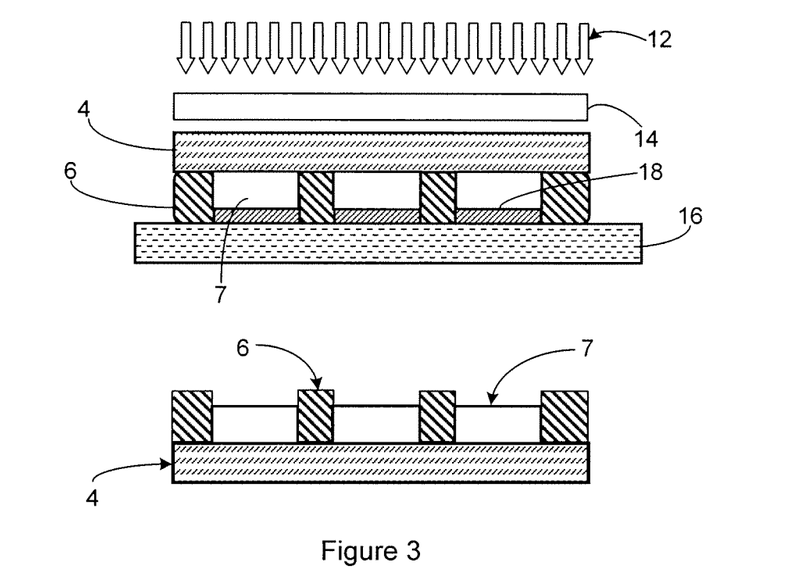
FIG. 3 is a schematic of fabrication of PEG hydrogel walls surrounding the micropallets of a micropallet array.

Particularly, as depicted in FIGS. 3 and 4, the methods described herein are used to manufacture solid or gel walls 6 that surround the micropallets 7. The walls 6 fill the cavities between the micropallets 7. The walls 6 provide or act as barriers to the deposition or attachment of cells or biomolecules 5 between the micropallets 7. By appropriately arranging the cavities, walls 6 of arbitrary shape and size can be prepared. The walls 6 can be made from materials in any other phase except gas phase, including solid, gel, hydrogel, liquid. The walls 6 can extend beyond the top surface of micropallets 7, be even in height with the micropallets 7, or be depressed relative to the micropallets 7.

The walls 6 can be produced by a variety of manufacturing methods. In one embodiment, as depicted in FIGS. 3 and 4, a micropatterned plate 3 comprising an array of micropallets 7 is first fabricated on a substrate surface 4. The light transmittance property of the material of the pallet 7 is different from that of the substrate material 4. As a result, an optical window exists between the micropallets 7 through which UV light 12 can be transmitted as it passes through the material of the substrate 4 but not the material of the micropallets 7. Thus the micropatterned plate 3 having an array of micropallets 7 acts as a mask to direct photopolymerization of hydrogel precursors on the substrate in the cavities between micropallets 7. After photopolymerization, hydrogel walls 6 are formed in the cavities between micropallets 7.

A variety of monomers can be selected to form the hydrogel walls 6, including poly(ethylene glycol) diacrylate, poly(ethylene glycol) dimethacrylate, poly(ethylene glycol) monomethoxyl acrylate, poly(ethylene glycol) monomethoxyl methacrylate, acrylic acid, acrylamide, 2-methacryloxy-ethyltrimethylammonium chloride, etc. A mixture of these monomers can also be used to form these hydrogel walls 6. By adjusting the ratio of these monomers, the properties of the hydrogel walls 6 can be adjusted. The properties include bulk properties such as softness, as well as surface properties such as hydrophobicity, electrical charge, protein adsorption, and cell attachment. In addition the hydrogels can be functionalized to contain other molecules such as proteins on the surface of or within the hydrogel.

Turning in detail to FIG. 3, the process to form a micropatterned plate 3 having an array of micropallets 7 surrounded with PEG hydrogel walls 6 preferably includes first placing the micropatterned plate 3 on a non-sticky silicon wafer 16, which is preferably coated with a perfluoroalkyl-silane, with the pallet side facing the silicon wafer 16. A liquid PEG precursor 18 composed of poly(ethylene glycol) diacrylate monomer, water and photoinitiator (50:50:0.5 wt:wt:wt) is then added at the edge of array of micropallets 7. The liquid tends to be spontaneously sucked into the gaps between the pallet 7 array and silicon wafer 16 by capillary force, forming an even liquid layer 18. Spacers can be inserted if the height of the gap needs to be accurately controlled.

This setup is then exposed to UV illumination 12 through a 325-nm shortpass filter 14. The light transmittance property of SU-8, the material from which the micropallets 7 is preferably formed, is different from that of glass, which is the material of the substrate 4 to which the micropallets 7 are attached. Glass starts to become opaque at around 270 nm, while the SU-8 film on glass starts to become opaque at around 350 nm. Therefore, due to the difference in UV transmittance between glass and SU-8, an optical window from 270 to 350 nm exists inside which glass is transparent while SU-8 is opaque. To create this optical window, a short-pass optical filter 14 at 325 nm is used. With the filter placed between array of micropallets 7 and the UV source 12, the pallets 7 block the UV light 12, while the inter-pallet area permits transmission of UV light 12. Thus, the PEG is photopolymerized in the inter-pallet space where UV light 12 was transmittable, but PEG 18 remained unreacted beneath the pallets 7 where UV light 12 was completely blocked. The array of micropallets 7 is then detached from silicon wafer 16, rinsed with water, and reversed.

In one experiment, the filter/glass/pallet array/PEG precursor/silicon wafer was exposed to a collimated UV light for 43-47 s. At UV-transmittable regions, i.e. inter-pallet space, the photoinitiator was decomposed into free radicals, which then initiated the polymerization reaction of PEG. Since each PEG monomer has two functional C=C groups, a highly cross-linked three-dimensional hydrogel is thus formed. On the space beneath the pallet, photoinitiator did not decompose and PEG precursor remains unreacted liquid state. After the reaction, the pallet array was detached from non-sticky silicon wafer, and rinsed with water to remove unreacted PEG precursor, and reversed.

Figure 5:
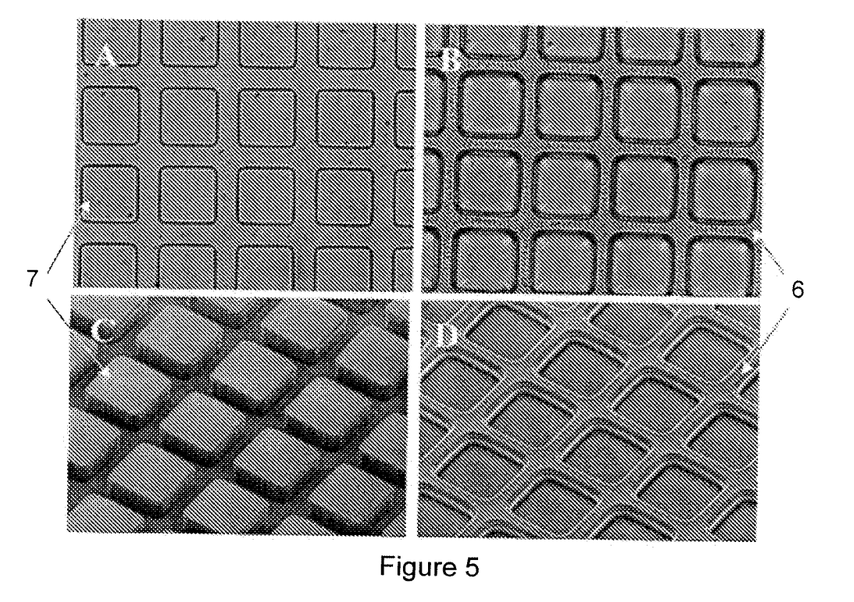

FIG. 5 shows PEG hydrogel walls 6 surrounding the micropallets 7. The images in FIG. 5 are optical (A, B) and SEM (C, D) images of an array of micropallets 7 (70-μm side, 30-μm height, 30-μm spacing) before (A, C) and after (B, D) fabrication of PEG hydrogel walls 6.

The embodiments described herein enable the patterning of cells or biomolecules at specific sites on the plate. In a preferred embodiment, the method is as follows: first, a plate is prepared containing an array of micropallets and the surrounded walls by any suitable manufacturing process, such as the manufacturing process described above. The walls themselves can be designed to possess surface properties that prevent protein adsorption and cell attachment, or the surface property of the walls can be chemically modified to be repellent to protein adsorption and cell attachment. Next, the plate is placed in solution containing cells in suspension. After some time, the cells sink to the plate surface. Cells that fall on walls will not be able to adhere to the surface. Cells that fall on micropallet surfaces will be able to adhere and grow. After a suitable period of time, the solution is washed and replaced with clean buffer. Cells that have adhered to the surface will remain, whereas cells that were left on walls will be removed. Thus, the resulting plate will contain cells in a patterned formation which facilities biochemical analysis of these cells.

In addition, the embodiments disclosed herein can enable isolating subsets of samples from a larger population of samples. Even surrounded with walls, the specific micropallet with selected cell or biomolecule can be removable from the array by a mechanical force such as that generated by a focused laser pulse. The released micropallet with the attached samples is thus collected.

Turning to the FIG. 1, a schematic is provided showing use of the micro-patterned plate 3. As depicted, the micro-patterned plate 3 is placed in a container 1 filled with a liquid 2 and submerged within the liquid 2. The liquid 2 preferable contains materials of interest, in this case, cells 5. As depicted in FIGS. 1 and 2, the plate 3 has an array of releasable micropallets 7 formed on a substrate 4 and surrounded by solid or gel walls 6 created in the cavities between the micropallets 7. The walls 6 are shown to extend above the top surface of micropallets 7. The walls 6 however could be even with or below the level of the pallets 7. Materials from the liquid, e.g., cells 5, sink and land on the surface of the plate 3. If the cells 5 land on surfaces of the micropallets 7 they may stick or react with the surface at that point. If they land on walls 6, they do not stick, but typically slide over to the micropallets 7. The walls 6, which fill the cavities between the micropallets 7, provide contiguous, impenetrable barriers preventing the attachment of cell 5 and other media on the surfaces of the cavities.

Figure 6:
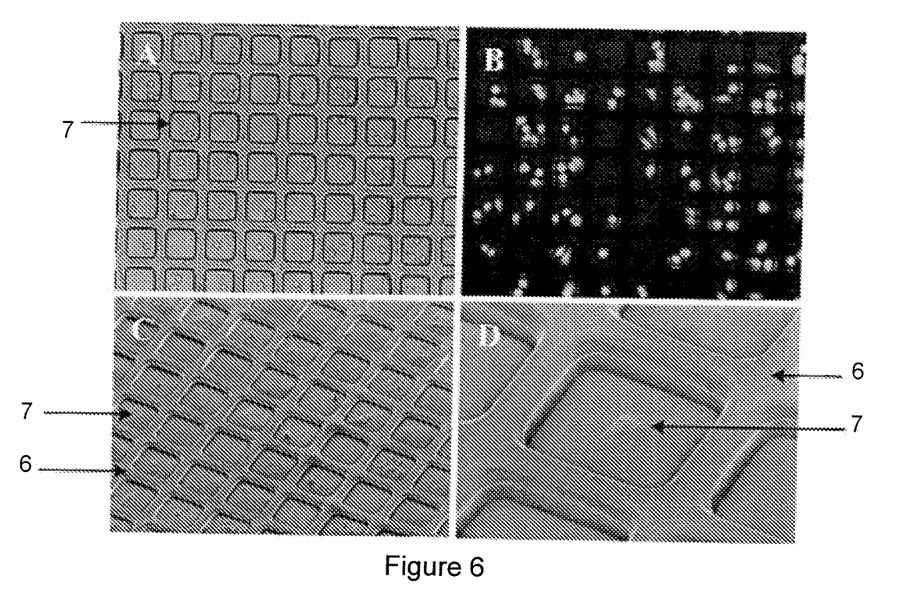
FIG. 6 depicts patterning of cells on micropallet arrays with PEG walls.

FIG. 6 provides images of patterning of cells on an array of micropallets 7 with PEG walls 6. HeLa cells in suspension were placed on the arrays (70-mm side, 30-mm height, 30-mm spacing) and allowed to grow for 16 h. Image (A) is a transmitted light image of HeLa cells grown on micropallets 7 in an array. Image (B) is a fluorescence image of cells loaded with the vital dye Oregon green. The image corresponds to the transmitted light image (A). Image (C) is a SEM image of cells grown on micropallets 7 in an array. Image (D) is a close view of a HeLa cell grown on a pallet 7.

To determine whether cells could be localized on the tops of the pallets, the micropallets 7 in an array with PEG walls 6 were coated with collagen for 2 h. HeLa cells were then cultured on the pallet 7 array in a standard tissue culture medium. The cells on the pallet 7 arrays were examined by microscopy after 6, 24 and 48 h and were shown to remain localized exclusively to the pallet 7 (FIG. 6A). No cells were identified on the PEG walls (n=500 cells). The cells remain on pallet region even after 3 days of incubation. For comparison, cells were cultured without PEG walls. Ninety-nine percent of the cells (n=500 cells) grew in random locations on the glass surface or the side walls of the pallets under these conditions. Without PEG walls, the cells were localized by gravitational forces to the region between the pallets. In contrast, with PEG walls, the HeLa cells attached exclusively to the portion of the pallet surface. Also the level of PEG walls is higher than that of pallet; gravitational forces also help the cells localize on the pallet surface. Although the cells grown on the pallet array appeared healthy on the basis of their morphology, a live-cell assay was carried out using the viability dye Oregon green (FIG. 6B). In this assay, viable cells were able to take up the diacetate form of the dye and metabolize it to the membrane impermeant free acid. After washing, viable cells exhibit the fluorescence of Oregon green. Nonviable cells are unable to metabolize or retain the dye and are nonfluorescent. HeLa cells grown on the array for 16 h took up and retained the fluorescent dye, indicating their viability. In addition, SEM images (FIGS. 6C and 6D) clearly show that the HeLa cells exclusively grew on pallet portion.

In addition, subsets of samples can be isolated from a larger population of samples. Even surrounded with walls, the specific micropallet with selected cell or biomolecule can be removable from the array by a mechanical force such as that generated by a focused laser pulse. The released micropallet with the attached samples is thus collected.

Figure 7:
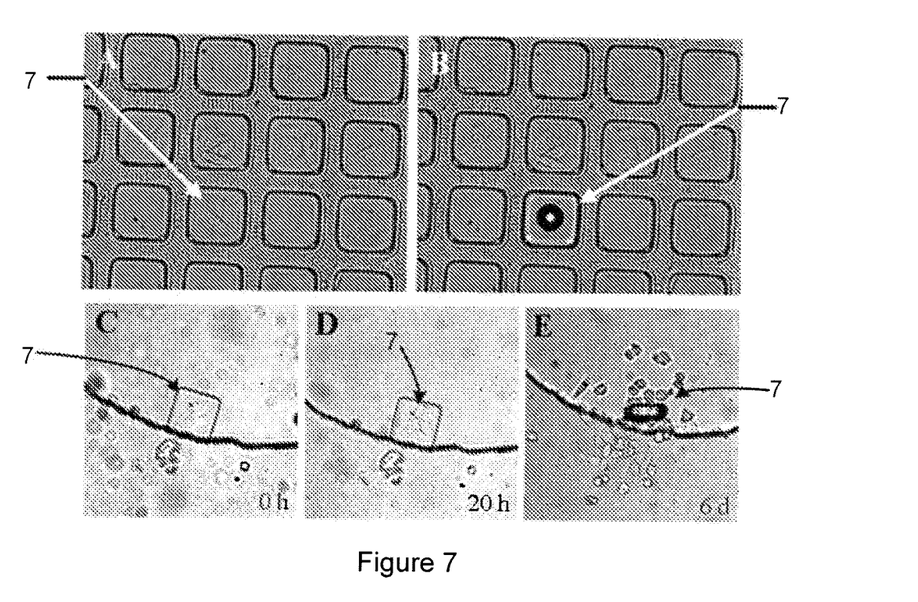
FIG. 7 depicts a single cell sorting on-chip.

FIG. 7 further shows that HeLa cells were cultured on pallet 7 arrays with PEG walls. The cells were localized to the pallet surfaces. A pallet 7 with a single cell was released by a focused laser pulse (8 µJ) (FIG. 6A, B). Following laser-based release, the detached pallet was collected in a multiwell plate. To determine the feasibility of collecting single cells for culture and expansion, pallets with single HeLa cells were released, collected, and placed into a multiwell plate. The cells were imaged (FIGS. 7C, D and E) by microscopy within 1 h of collection and then at varying times therefore. Within 1 h after collection, HeLa cells remained on the pallet tops (FIG. 7C). By 20 h after collection, cells had undergone cell division (FIG. 7D). Within 2-6 days following culture, a small colony of cells was present with cells attached to both the pallet and surrounding area (FIG. 7E). All cells in the colony were clones of the original single cell. The pallets were frequently observed to rotate which apparently was caused by the cell immigration and division. These data demonstrate the feasibility of collecting live HeLa cells from the pallet array and producing colonies of clonal cells.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed:

1. A micropatterned plate comprising:

a plate body, an array of a plurality of elevated sites extending from a surface of the plate body and releasably attached to the surface of the plate body, wherein the plurality of elevated sites are adapted to act as a carrier for biological material of interest adhered thereto when released from the surface of the plate body, wherein the plurality of elevated sites are releasable from the surface of the plate body leaving the structure of the plate body intact when one or more of the plurality of elevated sites is released from the surface of the plate body, and a plurality of walls separate from the plate body and extending from the surface of the plate body contiguously across the plate body in a criss-crossing configuration, wherein the plurality of walls fill cavities between each adjacent individual ones of the plurality of elevated sites in surrounding contact with individual ones of the plurality of elevated sites interposing and forming a barrier between individual ones of the plurality of elevated sites and preventing a fluid in contact with a top surface of the individual ones of the plurality of elevated sites from the cavities between each adjacent individual ones of the plurality of elevated sites, and wherein the plurality of walls are formed such that the biological material of interest adheres only to the plurality of elevated sites and wherein the plurality of elevated sites comprise a plurality of micro pallets.

2. The micropatterned plate of claim 1 wherein the plurality of walls are solid.

3. The micropaterened plate of claim 1 wherein the plurality of walls are formed from a gel.

4. The micropatterned plate of claim 1 wherein individual ones of the plurality of elevated sites are releasable from the surface of the plate body through application of a mechanical force.

5. The micropatterned plate of claim 1 wherein the plurality of walls are configured to prevent protein adsorption and cell attachment.

6. The micropatterned plate of claim 1 wherein the plurality of walls are configured to repel protein adsorption and cell attachment.

7. The micropatterned plate of claim 1 wherein the plurality of walls comprise a first material and the plate body comprises a second material, wherein the first and second materials are different materials.

8. The micropatterned plate of claim 7 wherein the plurality of elevated sites comprise a third material, wherein the second and third materials have differing light transmittance property wherein an optical window exists between the plurality of elevated sites to allow photopolymerization of the first material to form the plurality of walls between the plurality of elevated sites.

\* \* \* \* \*